(12) United States Patent
Cho et al.

(10) Patent No.: US 9,474,084 B2
(45) Date of Patent: Oct. 18, 2016

(54) MAC PROTOCOL IN WIRELESS BODY AREA NETWORK CAPABLE OF PROCESSING EMERGENCY DATA AND WIRELESS NETWORK COMMUNICATION METHOD USING SAME

(75) Inventors: Jinsung Cho, Gyeonggi-do (KR); Beom-Seok Kim, Gyeongbuk (KR)

(73) Assignee: UNIVERSITY-INDUSTRY COOPERATION GROUP OF KYUNG HEE UNIVERSITY, Gyeonggi-do (KR)

( * ) Notice: Subject to any disclaimer, the term of this patent is extended or adjusted under 35 U.S.C. 154(b) by 109 days.

(21) Appl. No.: 14/119,383

(22) PCT Filed: Dec. 8, 2011

(86) PCT No.: PCT/KR2011/009462
§ 371 (c)(1),
(2), (4) Date: Nov. 21, 2013

(87) PCT Pub. No.: WO2012/161396
PCT Pub. Date: Nov. 29, 2012

(65) Prior Publication Data
US 2014/0119257 A1    May 1, 2014

(30) Foreign Application Priority Data
May 25, 2011 (KR) .................. 10-2011-0049442

(51) Int. Cl.
| | | |
|---|---|---|
| *H04W 72/12* | (2009.01) | |
| *H04W 72/04* | (2009.01) | |
| *H04W 52/02* | (2009.01) | |
| *H04W 76/00* | (2009.01) | |
| *H04W 4/22* | (2009.01) | |
| *H04L 29/08* | (2006.01) | |
| *A61B 5/00* | (2006.01) | |

(52) U.S. Cl.
CPC ..... *H04W 72/1242* (2013.01); *H04W 52/0216* (2013.01); *H04W 72/0446* (2013.01); *H04W 76/007* (2013.01); *A61B 5/0024* (2013.01); *H04L 67/12* (2013.01); *H04W 4/22* (2013.01)

(58) Field of Classification Search
None
See application file for complete search history.

(56) References Cited

U.S. PATENT DOCUMENTS

2012/0063397 A1* 3/2012 Abedi ............... H04W 72/1205
370/329

OTHER PUBLICATIONS

Kim et al., "An Emergency Handling Scheme for Superframe-Structured MAC protocols in WBAN", 5th International Conference on Ubiquitous Information Management and Communication (ICUIMC2011), Feb. 23, 2011, pp. 1-3.*

(Continued)

*Primary Examiner* — Jamal Javaid
*Assistant Examiner* — George Atkins, Jr.
(74) *Attorney, Agent, or Firm* — Kinney & Lange, P.A.

(57) ABSTRACT

The present invention relates to a MAC protocol in a wireless body area network capable of processing emergency data and a wireless network communication method using the same. More specifically, the present invention replaces a Contention Free Period (CFP) of a WBAN MAC protocol with a Mixed Period (MP) for processing the emergency data, and sets an inactive period as an Extended Period (EP) for additional allocation due to the emergency data processing and re-allocation of a pre-guarantee Guaranteed Time Slot (GTS). As described above, the present invention can efficiently process the emergency data and enables emergency data processing which can guarantee low delay and high reliability of the emergency data.

10 Claims, 4 Drawing Sheets

(56) References Cited

OTHER PUBLICATIONS

Kim et al., "An Emergency Handling Scheme for Superfram-Structured MAC Protocols in WBAN", 5$^{th}$ International Conference on Ubiquitous Information Management and Communication (ICUIM2011), Feb. 23, 2011, pp. 1-3.*
International Search Report for International Application No. PCT/KR2011/009462, dated Jul. 30, 2012.
Kim, Beom Seok et al., "An Emergency Handling Scheme for Superframe-Structured MAC protocols in WBAN", 5th International Conference on Ubiquitous Information Management and Communication (ICUIMC2011), Feb. 23, 2011, pp. 1-3.
Bin Zhen et al., "NICT's MAC Proposal to IEEE 802.15.6-document", Nov. 14, 2009.
Arthur Astrin, "TG6 Draft; 15-10-0245-06-0006-tg6-draft", IEEE Draft; 15-10-0245-06-TG6-Draft. IEEE-SA Mentor. Piscataway, NJ, USA, vol. 802-156, No. 6, May 20, 2010, pp. 1-225, XP017665800.
Lee Myung et al., "Versatile MAC for Body Area Network Update for UWB PHY", May 4, 2009.
European Office Action dated Nov. 23, 2015, for corresponding European Application No. 11866072.9.

* cited by examiner

FIG. 4

| Algorithm of EP processing for coordinator |
|---|

```
         start of inactive period
1.     Additional_CAP_Count <- 0
2.     while (EP REQ Time != 0)
3.        if (receive CAP REQ)
4.           Insert CAP REQ information to CAP REQ List
5.        end of if
6.     end of while
7.     if (RE-ALLOC CFP List != NULL II CAP REQ List != NULL)
8.        Swich to Extended period (EP)
9.        Broadcast ACK message
10.       while (RE-ALLOC CFP List !=NULL)
11.          Dequeue from RE-ALLOC CFP List
12.          DATA Transmits
13.       end of while
14.       while (Additional_CAP_Count != 0)
15.          if (Inactive period time == 0)
16.             Additional_CAP_Count <-0
17.          else
18.             slotted-CSMA/CA operate
19.             Additional_CAP_Count--
20.          end of if
21.       end of while
22.    else
23.       Maintain Inactive period
24.    end of if
```

MAC PROTOCOL IN WIRELESS BODY AREA NETWORK CAPABLE OF PROCESSING EMERGENCY DATA AND WIRELESS NETWORK COMMUNICATION METHOD USING SAME

BACKGROUND

The present invention relates to a MAC protocol in a wireless body area network capable of processing emergency data and a wireless network communication method using the same, and more particularly, to a MAC protocol in a wireless body area network capable of processing emergency data and wireless network communication method using the same, which can efficiently process emergency data and guarantee low delay and high reliability of the emergency data by substituting a Contention Free Period (CFP) of the WBAN MAC protocol with a Mixed Period (MP) for processing the emergency data, and setting an inactive period as an Extended Period (EP) for reallocating a Guaranteed Time Slot (GTS) which is not additionally allocated and guaranteed due to processing of the emergency data.

The present invention relates to a MAC protocol in a wireless body area network capable of processing emergency data and a wireless network communication method using the same, which can process, in a body area within 3 m, emergency data appropriate for applications having different medical/non-medical characteristics and objects and a WBAN network system in which periodic or aperiodic characteristics of the applications are used together.

Following WLAN and WPAN techniques, the Wireless Body Area Network (WBAN) is spotlighted recently as a wireless technique for medical/non-medical communication in a body area.

The WBAN is a network capable of performing wireless communication within a body area. Here, the body area wireless communication refers to wireless communication in which terminals positioned inside or outside of a human body communicate with other devices placed within about 3 m.

The most outstanding characteristic of WBAN, distinguishing WBAN from other networks such as WLAN, WPAN and the like, is considering a medical device as a Killer item. Another outstanding characteristic of the WBAN is considering wireless communication of a human body transplanting type wireless device transplanted inside a human body.

Accordingly, WBAN is currently applied to a variety of uses and may be broadly divided into medical and non-medical wireless devices. That is, WBAN may be divided into a non-medical wireless device for communications between consumer electronics, a human body transplant type wireless device transplanted inside a human body to monitor a health state inside the human body or to handle a situation wherein an abnormal state occurs inside the human body, and an external wireless device for transmitting and receiving data to and from medical sensors placed within 3 m from the human body. A MAC protocol of such a WBAN should simultaneously satisfy characteristics of medical devices and consumer electronics.

The IEEE 802.15.4 ZigBee MAC protocol, which is a representative MAC protocol of WBAN, coordinates medium access of a device using a hybrid superframe structure which uses a beacon.

A superframe is divided into an active period for exchanging data between devices and an inactive period in which a device may operate in a sleep mode.

The active period is again divided into a Contention Access Period (CAP) where medium access is allowed through contention among devices and a Contention Free Period (CFP) where only selected devices may exchange data at a predetermined time point.

The ZigBee MAC protocol aiming at low power consumption and low transmission rate divides a period into 16 equal slots and is configured of a Contention Access Period (CAP) and a Contention Free Period (CFP), and the CFP configured of 7 Guaranteed Time Slots (GTSs) is in charge of guaranteed transmission.

Conventional ZigBee provides GTS allocation limited to 7. In the GTS period, resources are allocated in advance only to specific pre-selected devices, and thus devices other than the corresponding specific devices cannot transmit data. Accordingly, when 8 or more nodes request the GTS, the GTS may not be allocated to nodes excluding seven nodes.

Various methods for improving limitations in allocating GTS are invented in order to overcome the drawbacks of conventional ZigBee as described above, and have a common feature in that continuous allocation of GTS is dynamically or statically performed. In this case, the CFP grows to be large. In consideration of the characteristics of WBAN which provides medical services, reliably and rapidly processing emergency data is one very important requirement, and if the reserved CFP increases, delay time of the emergency data is extended.

SUMMARY

The present invention is conceived to solve the above problems, and one aspect of the present invention is to provide a MAC protocol in a wireless body area network capable of processing emergency data and a wireless network communication method using the same, which can efficiently process the emergency data and guarantee low delay and high reliability of the emergency data by substituting a Contention Free Period (CFP) of the WBAN MAC protocol with a Mixed Period (MP) for processing the emergency data, and setting an inactive period as an Extended Period (EP) for reallocating a Guaranteed Time Slot (GTS) which is not additionally allocated and guaranteed due to processing of the emergency data.

Another aspect of the present invention is to provide a MAC protocol in a wireless body area network capable of processing emergency data and a wireless network communication method using the same, which can guarantee flexibility and reliability of data transmission by providing an Extended Period (EP) for guaranteeing transmission of lost data, which may occur due to processing of the emergency data, and allocating an additional transmission slot.

In accordance with one aspect of the present invention, a MAC protocol in a wireless body area network capable of processing emergency data and a wireless network communication method using the same substitute a Mixed Period (MP) for processing emergency data for a Contention Free Period (CFP) of the WBAN MAC protocol, in the WBAN MAC protocol using a MAC of a superframe structure.

When a Guaranteed Time Slot (GTS) which is not additionally allocated and guaranteed occurs upon processing of the emergency data in the MP, an inactive period of the WBAN MAC protocol may be set as an Extended Period (EP) for reallocating the GTS which is not additionally allocated and guaranteed due to processing of the emergency data.

The MP may include a CAP slot and a GTS slot, and use a polling scheme to guarantee instantaneous processing of the emergency data.

The MP corresponding to the CFP of the MAC protocol having a superframe structure may include the CAP slot and the GTS slot such that the MP has two lengths.

The EP may include an ER-ACK period, a reallocated GTS period, and an additional CAP period.

A coordinator may process the emergency data using the WBAN MAC protocol having the MP and the EP.

The coordinator may reallocate a GTS to a node registered in the MP through the EP, and may receive a request for using a CAP from a node which needs additional transmission and processes to allow the additional transmission to be performed as long as a required time period.

The coordinator may provide priority-based CW (Contention Window) and CP (Contention Probability) values such that an emergency node which desires to process the emergency data during the MP may rapidly occupy a channel.

When the amount of the emergency data is larger than a previously set value, the coordinator may allow the emergency node to use the GTS, while inducing reallocation of the GTS in the EP by inserting information on a reserved node into a reallocated GTS list to guarantee transmission of the reserved node.

The coordinator may inform whether an emergency node uses the GTS, and may transmit a polling message at a start point of a GTS slot to reduce waste of power in a reserved node by reducing idle listening of the reserved node.

The coordinator may guarantee QoS of burst traffic by maintaining a count of a node which requires additional transmission through a period receiving an additional CAP request, at a start point of the EP.

When a sub-period requesting an additional CAP is ended, the coordinator may provide a node with a length of the EP by transmitting an ACK to the node, in which the ACK includes reallocation information in the reallocated GTS period, and information on a start time of the requested CAP.

The present invention has been devised to solve the problems described above, and is advantageous in that emergency data may be efficiently processed in WBAN and low delay and high reliability of the emergency data are guaranteed by substituting a CFP of the WBAM MAC protocol with an MP for processing the emergency data and applying a priority-based channel access method.

In addition, the present invention is advantageous in that high transplantation into a MAC protocol having a superframe structure can be pursued.

Further, the present invention is advantageous in that flexibility and reliability of data transmission may be guaranteed by providing an EP for guaranteeing transmission of lost data, which can occur due to processing of emergency data, and allocating an additional transmission slot.

BRIEF DESCRIPTION OF THE DRAWINGS

FIG. 4 is a diagram showing an execution algorithm of the extended period of FIG. 3.

DETAILED DESCRIPTION

Exemplary embodiments of a MAC protocol in a wireless body area network capable of processing emergency data and a wireless network communication method using the same according to the present invention will be described hereinafter in detail with reference to the accompanying drawings.

The WBAN MAC protocol using a MAC of a superframe structure according to the present invention has a Mixed Period (MP) for processing emergency data in a continuously allocated Contention Free Period (CFP) of the WBAN MAC protocol and an Extended Period (EP) for guaranteeing reliability of data, which can be lost due to processing of the emergency data, and allowing additional transmission of the lost data.

Figure 1:
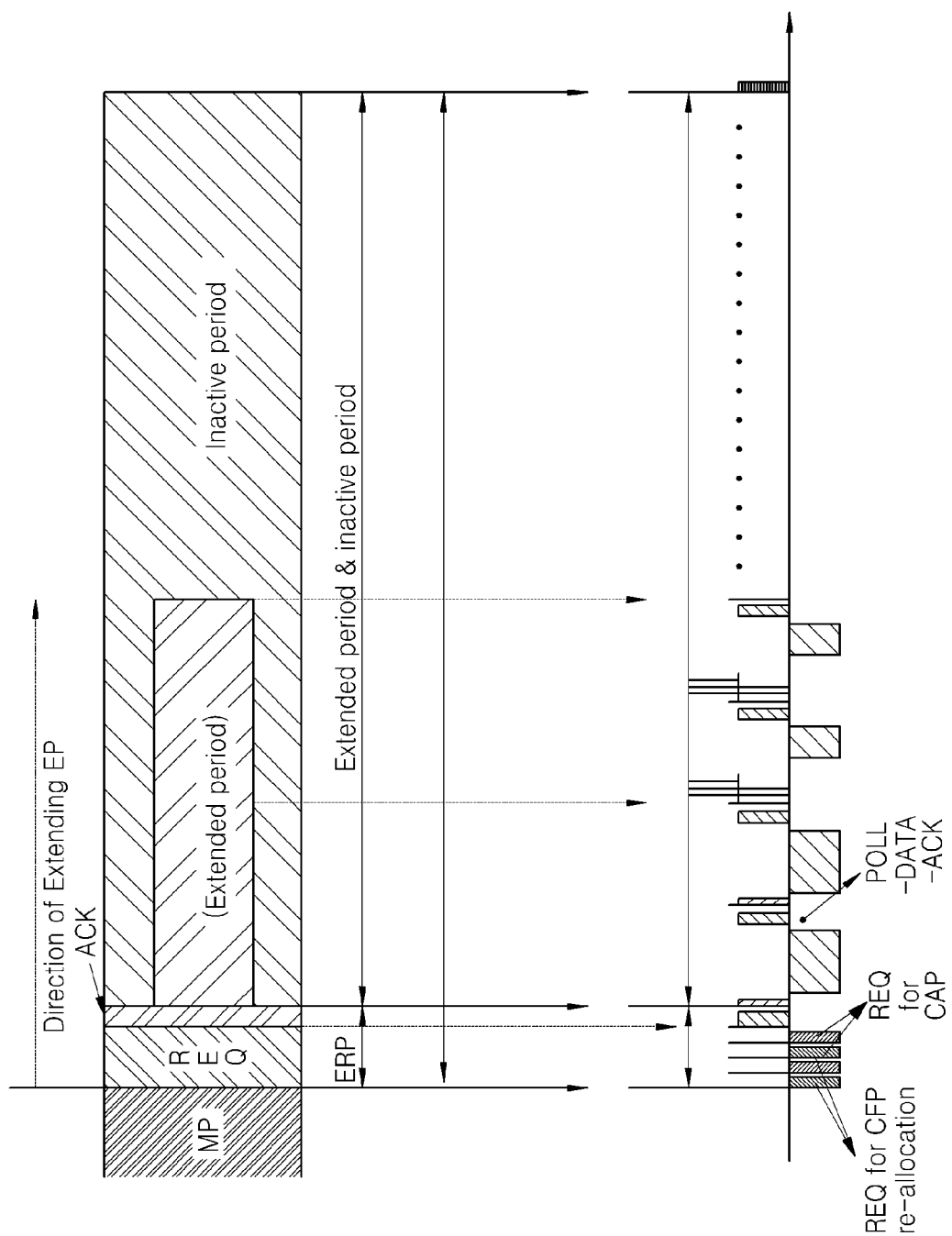
FIG. 1 is a diagram showing a mixed period of a MAC protocol in a wireless body area network according to one exemplary embodiment of the present invention.
Figure 2:
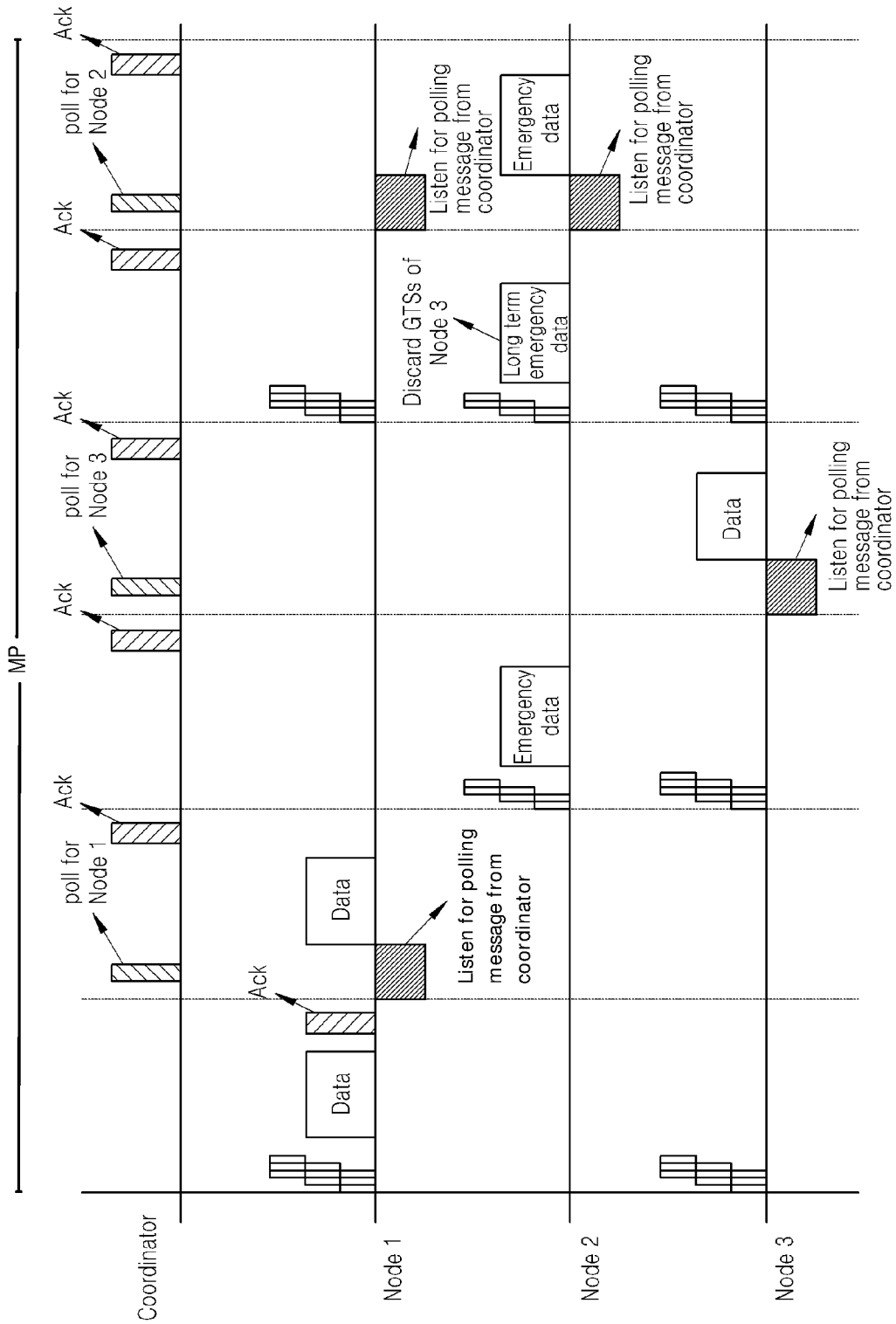
FIG. 2 is a diagram showing a procedure of processing emergency data in the mixed period of FIG. 1.

FIG. 1 is a diagram showing a mixed period of a MAC protocol in a wireless body area network according to one exemplary embodiment of the present invention, and FIG. 2 is a diagram showing a procedure of processing an emergency data in the mixed period of FIG. 1.

Referring to the figures, the MP is twice as long as a general CFP. This is because a unit of the MP is composed of a CAP slot and a GTS slot.

Generally, there are two reasons for using two slots as a unit.

First is to rapidly process emergency data. The present invention allows emergency data to be processed through contention by placing the CAP slot before the GTS slot. In addition, the present invention allows a GTS reserved through a beacon to be used for processing emergency data by using a polling scheme.

Second is to decrease delay of burst traffic. Since burst traffic cannot be transmitted during a continuous CFP, the burst traffic can be flexibly transmitted using CAP slots of the MP. As described above, the present invention may relieve the problems of the burst traffic through a priority-based channel access method.

Processing emergency data in the MP is divided into processing in the CAP slot and processing in the GTS slot.

A coordinator reallocates a GTS to a node which is registered in the MP through the EP, and receives a request for using a CAP from a node which needs additional transmission and processes to allow the additional transmission to be performed as long as a required time period.

In addition, the coordinator provides priority-based CW and CP values so that an emergency node which desires to process emergency data during the MP may rapidly occupy a channel.

That is, the present invention allows priority-based channel access by applying CW and CP policies of the IEEE 802.15.6 baseline draft for the process in the CAP slot and allows rapid channel access of the emergency data through the priority-based channel access.

If emergency data, which is not processed in the CAP slot, is present, the GTS slot, which is a latter part of the unit, is used to process the emergency data.

At this point, the GTS reserved through a beacon is added to a reallocation GTS list by the coordinator, and the coordinator sets the destination address of a polling message as an emergency node in the front part of the GTS.

The reason for using the polling scheme is that the polling scheme may be flexibly applied to all kinds of MAC protocols having a superframe structure, such as IEEE 802.15.6, and may avoid idle listening.

The polling message is transferred to both the emergency node and the reserved node, and the reserved node changes its own state to a sleep mode since the polling message is not for the reserved node itself, and the emergency node may process the emergency data using the GTS.

As such, the present invention is advantageous in that emergency data may be efficiently processed in the WBAN while low delay and high reliability of the emergency data are guaranteed by substituting the CFP of the WBAM MAC protocol with an MP for processing the emergency data and applying a priority-based channel access method.

FIG. 2 is an example of the emergency handling of an MP. In FIG. 2, node 1 and node 3 attempt to access the first CAP slot with their own CW or CP value [3]. Node 1 wins the contention and accesses the first CAP slot. The data from node 1 are not emergency data and the next CFP slot is used by a reserved node. At the second CAP slot, node 2 and node 3 attempt to access the CAP. The data from node 2 have high priority emergency information that corresponds to both the CW and CP values. Therefore, node 2 uses the second CAP slot. The emergency data of node 2 is able to function with a single slot and the reserved node 3 can then use the next CFP slot. At the third CAP slot, node 1, node 2, and node 3 want to access the CAP slot. Node 1 and node 3 do not have emergency data, but node 2 has emergency data with a request for a long-term transmission. Due to its priority, the CW and CP values, and the request for long-term transmission, node 3 takes the CAP slot and reserves the CFP for node 1 that is discarded by the coordinator.

Figure 3:
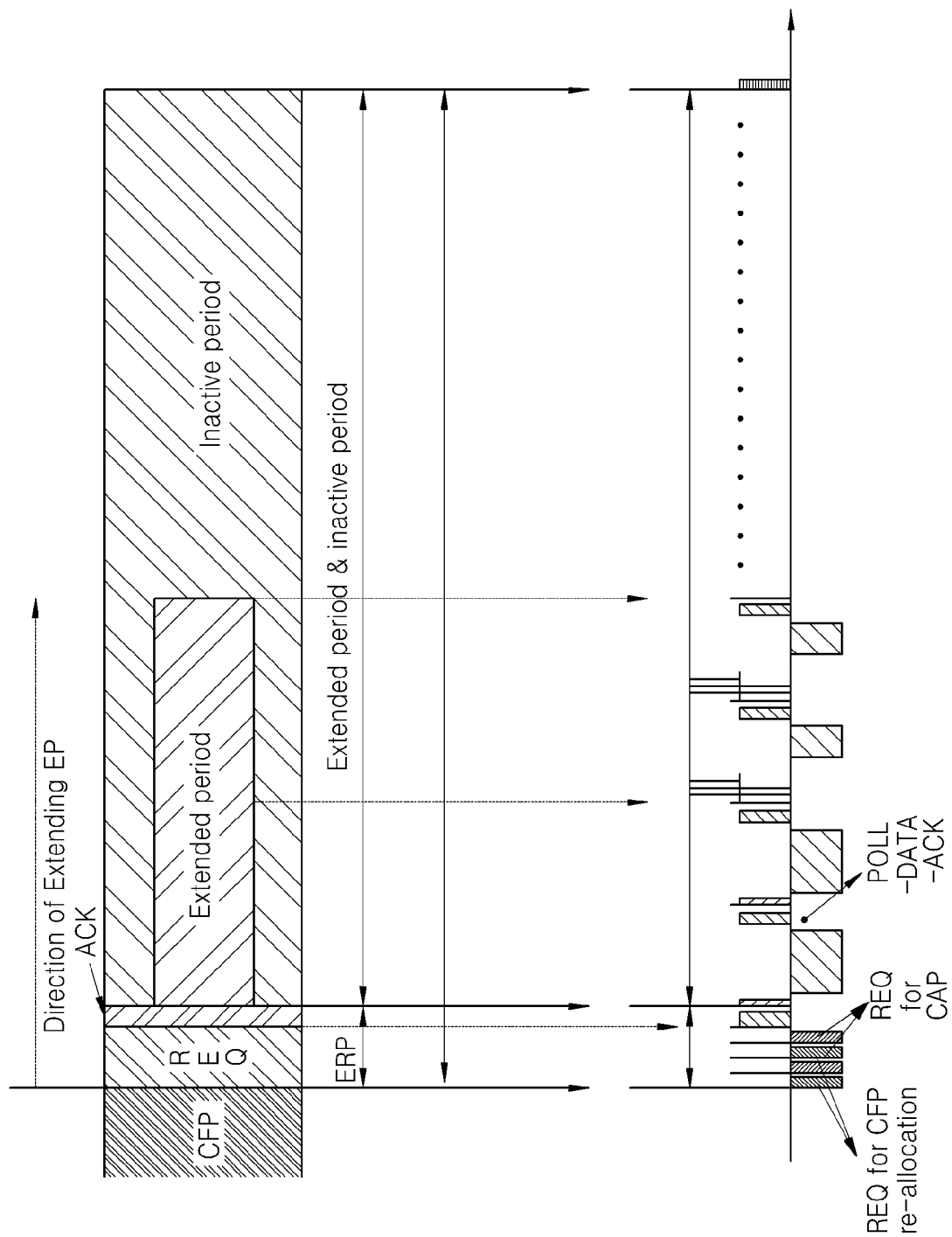
FIG. 3 is a diagram showing an extended period of a MAC protocol in a wireless body area network according to one exemplary embodiment of the present invention.

FIG. 3 is a diagram showing an extended period of a MAC protocol in a wireless body area network according to one exemplary embodiment of the present invention, and FIG. 4 is a diagram showing an execution algorithm of the extended period of FIG. 3.

Referring to the figures, a GTS slot, which is not guaranteed due to processing of emergency data, may be generated in the EP according to the present invention. In addition, QoS of burst traffic may not be guaranteed due to the CAP relatively shortened due to allocation of the GTS.

Thus, in order to solve the problems described above, the present invention switches an inactive period to an EP.

The EP has an ER-ACK period, a reallocated GTS period, and an additional CAP period.

A node may request use of an additional CAP slot in the EP through the ER-ACK period, which is the first period of the EP, and the coordinator provides information on the start time of the additional CAP through an ACK message. That is, the coordinator informs whether the emergency node uses the GTS, and transmits a polling message at the start point of the GTS slot in order to reduce waste of power in the reserved node by reducing idle listening of the reserved node.

A GTS not guaranteed and registered in the reallocated GTS list during the MP is reallocated in the reallocated GTS period, and emergency data is not processed in this period.

The reason why emergency data is not processed is that emergency data are generated consecutively. Generally, if an abnormal state occurs in a part of a human body, it will seriously affect the other parts of the human body. If an emergency situation occurs in an active period, the length of the reallocated GTS list is extended, and use of the additional CAP in the ER-ACK is increased, and thus utilization of the EP is enhanced. In addition, emergency data may be instantaneously processed through a priority-based channel access policy in the additional CAP.

For the reasons as described above, requirements as to processing of emergency data may be satisfied although the emergency data is not processed in the reallocated GTS period.

The additional CAP determines a length of the period by maintaining a count of the CAP slot requested through the ER-ACK period.

If the count of the CAP slot is larger than the remaining inactive period, the entire remaining inactive period is used as an additional CAP slot of the EP, otherwise, the EP is switched back to an inactive period for low power consumption when the count value of the CAP slot becomes zero.

In summary, if the sub-period requesting an additional CAP is ended, the coordinator provides a node with the length of the EP by transmitting an ACK, which includes reallocation information in the reallocated GTS period, and information on the start time of the requested CAP, to the node.

As described above, the present invention is advantageous in that flexibility and reliability of data transmission can be guaranteed by providing an EP for guaranteeing transmission of lost data, which may occur due to processing of emergency data, and allocating an additional transmission slot.

On the other hand, the present invention defines a near field communication scheme for medical devices and consumer electronics. The present invention may allow real-time remote diagnoses/prescriptions through lower power consumption and guaranteed data transmission using the near field communication scheme, and may allow non-medical services (e.g., moving images, mp3 files, portal services, and the like). The present invention may prepare a framework for simultaneously providing various services by utilizing the characteristics as described above, and may promote reduction in manufacturing cost of an enterprise and user convenience. Furthermore, the present invention may allow efficient diagnoses and prescriptions for residents, seniors and disabled persons who are not provided with medical services and enable prompt treatment when an emergency situation occurs.

The present invention has been described with reference to some exemplary embodiments. However, it will be understood by those skilled in the art that the present invention is not limited to specific embodiments, and various modifications, changes, alterations and equivalent embodiments can be made without departing from the scope of the present invention. Therefore, the scope and sprit of the present invention should be defined only by the accompanying claims and equivalents thereof.

The invention claimed is:

1. A Wireless Body Area Network (WBAN) comprising:
   a plurality of wireless communication devices located inside or outside of a human body, the wireless communication devices being located or capable of being located within 3 meters of the human body; and
   a coordinator device configured to coordinate communication with the plurality of wireless communication devices according to a Media Access Control (MAC) protocol using a MAC of a superframe structure, the MAC protocol being capable of processing emergency data,
   wherein the MAC protocol includes a Mixed Period (MP) for processing the emergency data that substitutes for a Contention Free Period (CFP) of the MAC protocol,
   wherein, when a Guaranteed Time Slot (GTS) which is not additionally allocated and guaranteed occurs upon processing of the emergency data in the MP, an inactive period of the WBAN MAC protocol is set as an Extended Period (EP) for reallocating the GTS which is not additionally allocated and guaranteed due to processing of the emergency data.

2. A Wireless Body Area Network (WBAN) comprising:
a plurality of wireless communication devices located inside or outside of a human body, the wireless communication devices being located or capable of being located within 3 meters of the human body; and
a coordinator device configured to coordinate communication with the plurality of wireless communication devices according to a Media Access Control (MAC) protocol using a MAC of a superframe structure, the MAC protocol being capable of processing emergency data,
wherein the MAC protocol includes a Mixed Period (MP) for processing the emergency data that substitutes for a Contention Free Period (CFP) of the MAC protocol, wherein the MP comprises a Contention Access Period (CAP) slot and a Guaranteed Time Slot (GTS), and uses a polling scheme to guarantee instantaneous processing of the emergency data.

3. The WBAN according to claim 2, wherein the MP corresponding to the CFP of the MAC protocol having a superframe structure comprises the CAP slot and the GTS slot.

4. The WBAN according to claim 1, wherein the EP includes an Emergency Response-Acknowledge (ER-ACK) period, a reallocated GTS period, and an additional CAP period.

5. A Wireless Body Area Network (WBAN) comprising:
a plurality of wireless communication devices located inside or outside of a human body, the wireless communication devices being located or capable of being located within 3 meters of the human body; and
a coordinator device configured to coordinate communication with the plurality of wireless communication devices according to a Media Access Control (MAC) protocol using a MAC of a superframe structure, the MAC protocol being capable of processing emergency data,
wherein the MAC protocol includes a Mixed Period (MP) for processing the emergency data that substitutes for a Contention Free Period (CFP) of the MAC protocol, wherein the coordinator device reallocates a Guaranteed Time Slot (GTS) to a node registered in the MP through an Extended Period (EP), and receives a request for using a Contention Access Period (CAP) from a node which needs additional transmission and processes to allow the additional transmission to be performed as long as a required time period.

6. The WBAN according to claim 5, wherein the coordinator device provides priority-based Contention Window (CW) and Contention Period (CP) values such that an emergency node which desires to process the emergency data during the MP may rapidly occupy a channel.

7. The WBAN according to claim 6, wherein, when the amount of the emergency data is larger than a previously set value, the coordinator device allows the emergency node to use the GTS, while inducing reallocation of the GTS in the EP by inserting information on a reserved node into a reallocated GTS list to guarantee transmission of the reserved node.

8. The WBAN according to claim 5, wherein the coordinator device informs whether an emergency node uses the GTS, and transmits a polling message at a start point of a GTS slot to reduce waste of power in a reserved node by reducing idle listening of the reserved node.

9. The WBAN according to claim 5, wherein the coordinator device guarantees Quality of Service (QoS) of burst traffic by maintaining a count of a node which requires additional transmission through a period receiving an additional CAP request, at a start point of the EP.

10. The WBAN according to claim 5, wherein, when a sub-period requesting an additional CAP is ended, the coordinator device provides a node with a length of the EP by transmitting an acknowledgement (ACK) to the node, the ACK including reallocation information in the reallocated GTS period, and information on a start time of the requested CAP.

* * * * *